(12) United States Patent
Ryan et al.

(10) Patent No.: US 8,053,244 B2
(45) Date of Patent: Nov. 8, 2011

(54) MAGNETIC OSCILLATOR BASED BIOSENSOR

(75) Inventors: Pat J. Ryan, St. Paul, MN (US); Haiwen Xi, Prior Lake, MN (US); Insik Jin, Eagan, MN (US)

(73) Assignee: Seagate Technology LLC, Scotts Valley, CA (US)

( * ) Notice: Subject to any disclaimer, the term of this patent is extended or adjusted under 35 U.S.C. 154(b) by 614 days.

(21) Appl. No.: 12/190,687

(22) Filed: Aug. 13, 2008

(65) Prior Publication Data

US 2010/0039105 A1 Feb. 18, 2010

(51) Int. Cl.
*G01N 27/00* (2006.01)
*G01N 27/72* (2006.01)
*G01N 33/543* (2006.01)
*G01N 33/551* (2006.01)

(52) U.S. Cl. ........ 436/149; 436/501; 436/518; 436/524; 436/526; 435/7.1; 422/82.01; 324/226; 324/228; 324/236

(58) Field of Classification Search ............ 436/94, 436/149, 150, 501, 518, 524, 526; 435/6, 435/7.1; 422/82.01; 324/226, 228, 236
See application file for complete search history.

(56) References Cited

U.S. PATENT DOCUMENTS

| | | | | |
|---|---|---|---|---|
| 5,981,297 | A * | 11/1999 | Baselt | 436/514 |
| 6,468,809 | B1 * | 10/2002 | Prinz et al. | 436/526 |
| 2005/0100930 | A1 | 5/2005 | Wang et al. | |
| 2008/0032423 | A1 | 2/2008 | Wang et al. | |
| 2009/0302953 | A1 * | 12/2009 | Xi et al. | 331/60 |

FOREIGN PATENT DOCUMENTS

WO WO 01/57506 8/2001

OTHER PUBLICATIONS

Wang et al., "Towards a Magnetic Microarray for Sensitive Diagnostics", Journal of Magnetism and Magnetic Materials 293 (2005) 731-739.
Han et al., "CMOS Integrated DNA Microarray Based on GMR Sensors", 2006 IEEE.
Han et al., "A High-Density Magnetoresistive Biosensor Array with Drift-Compensation Mechanism", 2007 IEEE International Solid-State Circuits Conference.
Xi et al., "Circular Domain Wall Motion Driven by Spin-Polarized Currents in Confined Square Nanomagnets", Journal of Applied Physics 97, 044306 (2005).
Kiselev et al., "Microwave Oscillations of a Nanomagnet Drive by a Spin-Polarized Current", 2003 Nature Publishing Group.
J. Grollier, "Synchronization of Spin-Transfer Oscillators Driven by Stimulated Microwave Currents", Physical Review B 73, 060409(R) (2006).
Kaka et al., "Mutual Phase-Locking of Microwave Spin Torque Nano-Oscillators", 2005 Nature Publishing Group.

* cited by examiner

*Primary Examiner* — Maureen Wallenhorst
(74) *Attorney, Agent, or Firm* — Campbell Nelson Whipps LLC

(57) ABSTRACT

A biosensor is described. The biosensor includes a fixed multilayer stack providing a magnetization oscillation, a voltage source electrically coupled to the fixed multilayer stack, and a binding molecule covalently bonded to the biosensor. The voltage source provides a direct current through the fixed multilayer stack to generate the magnetization oscillation and a target molecule including a magnetic nanoparticle forms a complex with the binding molecule and alters the magnetization oscillation.

20 Claims, 7 Drawing Sheets

_US 8,053,244 B2_

MAGNETIC OSCILLATOR BASED BIOSENSOR

BACKGROUND

Biosensing is under current research and development for a wide range of applications in the field of functional genomics and molecular diagnostics, for example. One technique uses fluorescent labels, which are optically detected with laser scanners. However, the required instrumentation needs to be reduced in size and cost to realize a hand-held device. Preferred sensing systems have high sensitivity, rapid response, portability, and low cost, preferably not requiring DNA amplification process. In addition, the biosensing system is desired to be compatible with CMOS processing, and can be easily integrated with a CMOS chip to form a lab-on-a-chip system.

Biosensing using magnetic microarrays has been proposed. The basic methodology of such a magnetic microarray is that a single-stranded DNA with a known sequence is immobilized (bound) on the sensor surface through a sulfur-Au linkage. Meanwhile, a tagging process using single-domain high-moment magnetic nanoparticles as tags are attached to targeted DNA fragments. When the tagged DNA fragments are selectively captured by complementary DNA probes that are attached to the sensors, the stray field of the magnetic nanoparticles is read out by the magnetic sensors. A giant magnetoresistive spin-valves or magnetic tunnel junction is used for magnetic field sensing.

One problem with these biosensors is that the sensing suffers from a large 1/f noise coming from the sensors themselves and from the MOS switches. There is a need for a biosensor that reduces 1/f noise without increasing the complexity of the system by implementing a frequency modulation scheme.

BRIEF SUMMARY

The present disclosure relates to a magnetic oscillator based biosensor. In particular, the magnetic oscillator based biosensor can be utilized alone or in a sensor array or biochip. Molecules such as, for example, DNA or RNA strands are detected by the oscillation frequency change of the magnetic oscillator based biosensor by the presence of these molecules tagged with magnetic nanoparticles. Since the oscillation resides in the GHz regime, the 1/f noise is reduced or avoided.

In an illustrative embodiment, a biosensor includes a fixed multilayer stack providing a magnetization oscillation, a voltage source electrically coupled to the fixed multilayer stack, and a binding molecule covalently bonded to the biosensor. The voltage source provides a direct current through the fixed multilayer stack to generate the magnetization oscillation and a target molecule including a magnetic nanoparticle forms a complex with the binding molecule and alters the magnetization oscillation.

In another illustrative embodiment, a biosensor array includes a plurality of detection sites disposed on a substrate and a voltage source electrically coupled to the detection sites. The voltage source provides a direct current to the detection sites. At least selected detection sites include a fixed multilayer stack generating a magnetization oscillation upon passing a spin polarized direct current through the fixed multilayer stack, and a binding molecule covalently bonded to the biosensor. A target molecule includes a magnetic nanoparticle that forms a complex with the binding molecule and alters the magnetization oscillation.

An illustrative method of detecting a magnetic complex in a sample includes the steps of passing a current through a fixed multilayer stack, generating a magnetization oscillation with the fixed multilayer stack with the current and detecting the magnetization oscillation. Then the method includes forming a magnetic complex with a target molecule. The target molecule includes a magnetic nanoparticle. A binding molecule is covalently bonded to the biosensor. Then the method includes detecting if the magnetization oscillation has been altered with the magnetic complex to form an altered magnetization oscillation to determine the presence of the target molecule.

BRIEF DESCRIPTION OF THE DRAWINGS

The disclosure may be more completely understood in consideration of the following detailed description of various embodiments of the disclosure in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
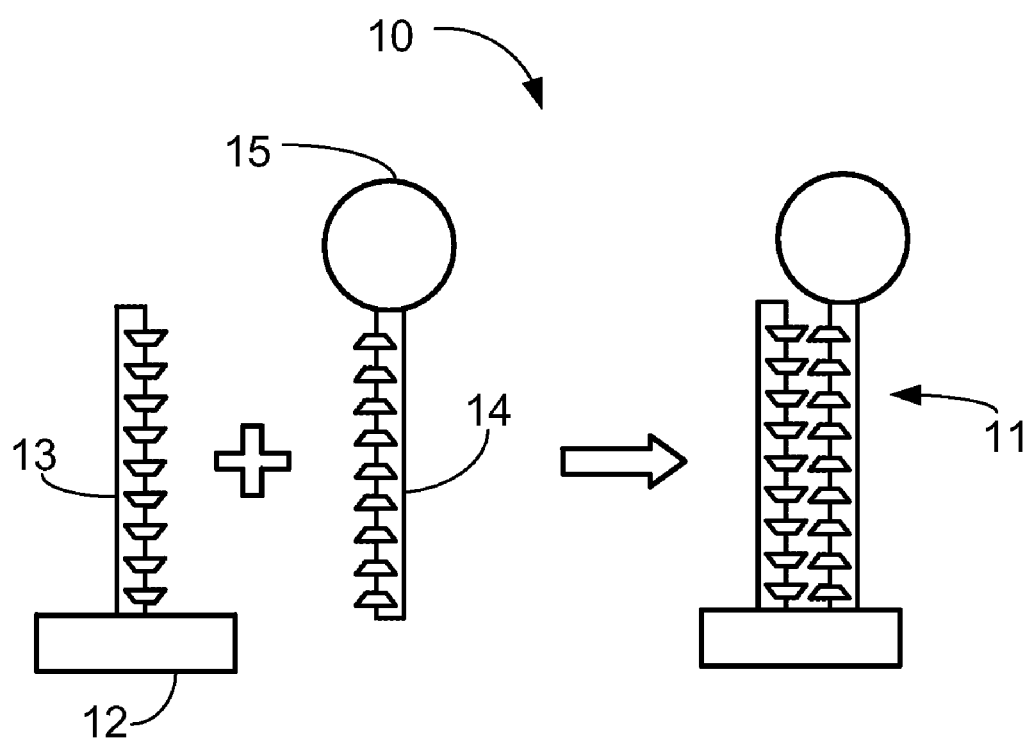
FIG. 1 is a schematic diagram of an illustrative biosensor detecting a target molecule.

In the following description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

A "binding molecule" refers to antibodies, strands of polynucleic acids (DNA or RNA), and molecular receptors capable of selectively binding to or 'recognizing' potential target molecules such as, for example, polynucleic acids, enzymes, proteins, peptides, antibodies, lipids, polymers, metal ions, and low molecular weight organic and inorganic species such as toxins, drugs (both prescription and illicit), explosives, and biohazards.

A "target molecule" refers to the molecule, molecular species, or organism whose presence, absence, or concentration the assay in question actually determines. Target molecules included include but are not limited to viruses, bacteria, other biological organisms such as fungi, antibodies, proteins, peptides, polynucleic acids, lipids, polymers, pharmaceutical compounds, organic compounds, biohazardous compounds, explosive compounds, and toxins, among others.

The present disclosure relates to a magnetic oscillator based biosensor. In particular, the magnetic oscillator based biosensor can be utilized alone or in a sensor array or biochip. Molecules such as, for example, DNA or RNA strands are detected by the oscillation frequency change of the magnetic oscillator based biosensor by the presence of these molecules tagged with magnetic nanoparticles. Since the oscillation resides in the GHz regime, the 1/f noise is reduced or avoided. While the present disclosure is not so limited, an appreciation of various aspects of the disclosure will be gained through a discussion of the examples provided below.

FIG. 1 is a schematic diagram of an illustrative biosensor 10. The biosensor 10 includes a magnetic field detector 12 and a binding molecule 13 covalently bonded to the biosensor 10. In many embodiments, the binding molecule 13 is covalently bonded to the magnetic field detector 12 or adjacent to the magnetic field detector 12. A target molecule 14 can be tagged with a magnetic nanoparticle 15. This tagged target molecule 14 can then be selectively bound to the binding molecule 13 to form a complex 11. For example, the binding molecule 13 can be a nucleic acid strand, and the tagged target molecule 14 can be a nucleic acid strand having a complementary sequence that hybridizes to a complex 11. The detector 12 can then interrogate the complex (described below) to determine the presence, absence, or concentration of the assay in question.

Useful nanoparticles includes magnetic (i.e., ferromagnetic) colloidal materials and particles. The magnetic nanoparticles can be high moment magnetic nanoparticles which are small in size so as to be superparamagnetic, or synthetic antiferromagnetic nanoparticles which contain at least two layers of antiferromagnetically-coupled high moment ferromagnets. Both types of nanoparticles appear "nonmagnetic" in the absence of magnetic field, and do not normally agglomerate. In many embodiments, magnetizable nanoparticles suitable for use include one or more materials selected from the group consisting of paramagnetic, superparamagnetic, ferromagnetic, and ferrimagnetic materials, as well as combinations thereof.

The magnetic nanoparticles preferably possess the following properties: (1) their remnant magnetization is as small as possible so that they preferably will not agglomerate in solutions (either superparamagnetic particles or antiferromagnetic particles can satisfy this requirement); (2) the tags display high magnetic moments under a modest magnetic field of about 100 Oe so they can be readily detected; (3) the size of the tags preferably is comparable to the target biomolecules so that they do not interfere with the DNA hybridization process and other biological processes; (4) the tags preferably are uniform and chemically stable in a biological environment; and/or (5) the tags preferably are biocompatible, i.e., water soluble and functionalized so that they are readily attached to DNA fragments or other biomolecules.

In many embodiments, the nanoparticles are high moment magnetic nanoparticles such as Co, Fe or CoFe nanocrystals which are superparamagnetic at room temperature. They can be fabricated by chemical routes such as salt reduction or compound decomposition in appropriate solutions. These particles can be synthesized with controlled size (e.g., 5-12 nm), are monodisperse, and are stabilized with oleic acid.

Magnetic nanoparticles and nanopowders suitable for use include but are not limited to Co, Co alloys, ferrites, Cobalt nitride, Cobalt oxide, Co—Pd, Co—Pt, Iron, Iron alloys, Fe—Au, Fe—Cr, Fe—N, $Fe_3O_4$, Fe—Pd, Fe—Pt, Fe—Zr—Nb—B, Mn—N, Nd—Fe—B, Nd—Fe—B—Nb—Cu, Ni, and Ni alloys. Alternatively and equally acceptable, a thin layer of gold can be plated onto a magnetic core, or a poly-L-lysine coated glass surface can be attached to a magnetic core. Some suitable nanoparticles are commercially available from, e.g., Nanoprobes, Inc. (Northbrook, Ill.), and Reade Advanced Materials (Providence, R.I.).

The size of the magnetic nanoparticles suitable for use is preferably comparable to the size of the target biomolecule to be worked with, such that the nanoparticles do not interfere with biological processes such as DNA hybridization. Consequently, the size of the magnetic nanoparticles can be from about 5 nm to about 250 nm (mean diameter), or from about 5 nm to about 150 nm, or from about 5 nm to about 20 nm. For example, magnetic nanoparticles having a mean diameter of 5 nm, 6 nm, 7 nm, 8 nm, 9 nm, 10 nm, 11 mm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 55 nm, 60 nm, 70 nm, 80 nm, 90 nm, 100 nm, 110 nm, 120 nm, 130 nm, 140 nm, and 150 nm, as well as nanoparticles having mean diameters in ranges between any two of these values, are suitable for use herein. Further, in addition to the more common spherical shape of magnetic nanoparticles, nanoparticles suitable for use with the present invention can be disks, rods, coils, or fibers.

Figure 2:
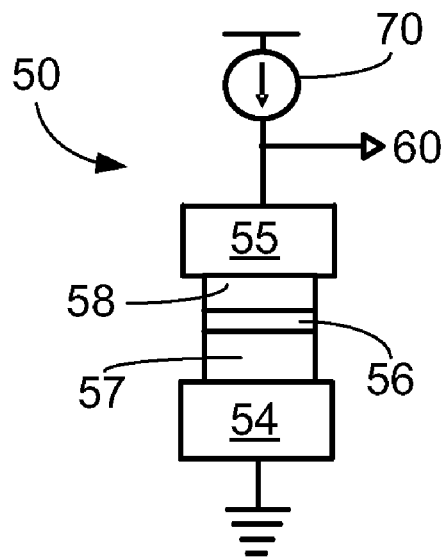
FIG. 2 is a schematic circuit diagram of an illustrative magnetic oscillator.

FIG. 2 is a schematic circuit diagram of an illustrative magnetic oscillator 50. The magnetic oscillator 50 includes a fixed multilayer stack that provides a magnetization oscillation. The fixed multilayer stack can have any useful configuration that produces a magnetization oscillation. A few embodiments of the fixed multilayer stack are illustrated in FIGS. 2-9 described herein. A current passing through the fixed multilayer stack causes the fixed multilayer stack to generate the magnetization oscillation. In some embodiments, the fixed multilayer stack has a magnetic layer with a fixed magnetization to spin polarize direct current passing through the magnetic layer. In other embodiments, a spin polarized current passes through the fized multilayer stack. The spin polarized current exerts a spin torque on a magnetic layer having a "free" magnetization and excites magnetization oscillation. In other embodiments, spin polarized current is passed through the fixed multilayer stack. The spin polarized current exerts a spin torque on a magnetic layer having a "free" magnetization and excites magnetization oscillation.

The illustrated magnetic oscillator 50 includes a fixed multilayer stack including a non-magnetic barrier or spacer layer 56 separating a fixed or pinned magnetic layer 57 and a free magnetic layer 58. This fixed multilayer stack is electrically between first electrode 54 and a second electrode 55. The free layer 58 has no or little coercivity or less magnetic volume, relative to the fixed layer 57, and its magnetization can be excited by the current, such as in the form of magnetization rotation/precession or spinwave, at a frequency that is a function of the current flowing through the fixed multilayer stack. Current is provided by a voltage source 70. The current is a direct current. The magnetization oscillation can be readout at an output 60 in the form of alternating current (AC) voltage. The fixed or pinned magnetic layer 57 can be either a single magnetic layer with a large coercivity or a magnetically soft layer pinned by an antiferromagnetic layer such as, for example, a synthetic antiferromagnetically coupled structure. The fixed multilayer stack can be a stack with a metallic spacer, a current-constrained path spacer, or an oxide barrier. Thus, the resistance of the fixed multilayer stack can vary in a wide range to match the impedance of the peripheral circuitry.

Figure 3:
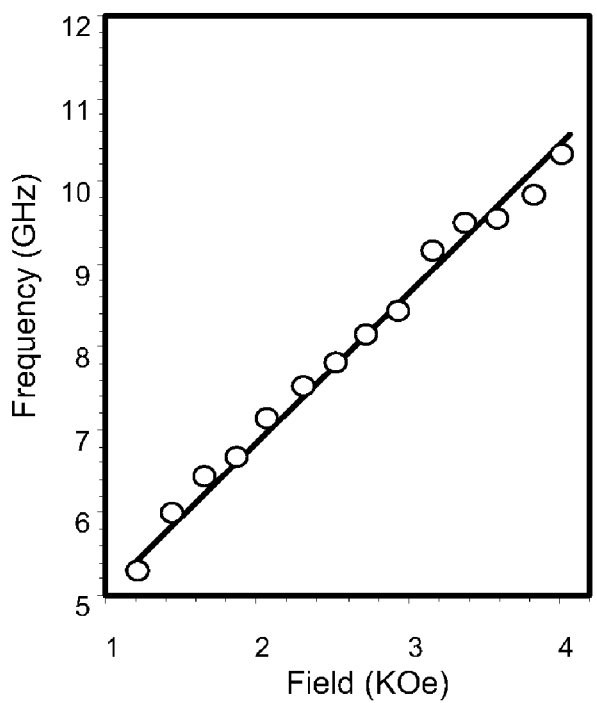
FIG. 3 is a graph illustrating the magnetization oscillation frequency as a function of the current flowing through the exemplary fixed multilayer stack shown in FIG. 2.

When a DC current is driven into the fixed multilayer stack (i.e., magnetic pillar), an AC voltage difference with a radio frequency appears across the stack due to the spin-torque transfer effect, that means some kind of magnetization precession is excited by the current in the free layer, which is translated to the AC voltage. FIG. 3 shows the magnetic field dependence of the oscillation frequency. With these characteristics, biosensing can be implemented with the magnetic nano-oscillators as the detector in FIG. 1. The radio frequency can be generated with and without magnetic field bias of the nano-oscillators.

Figure 4:
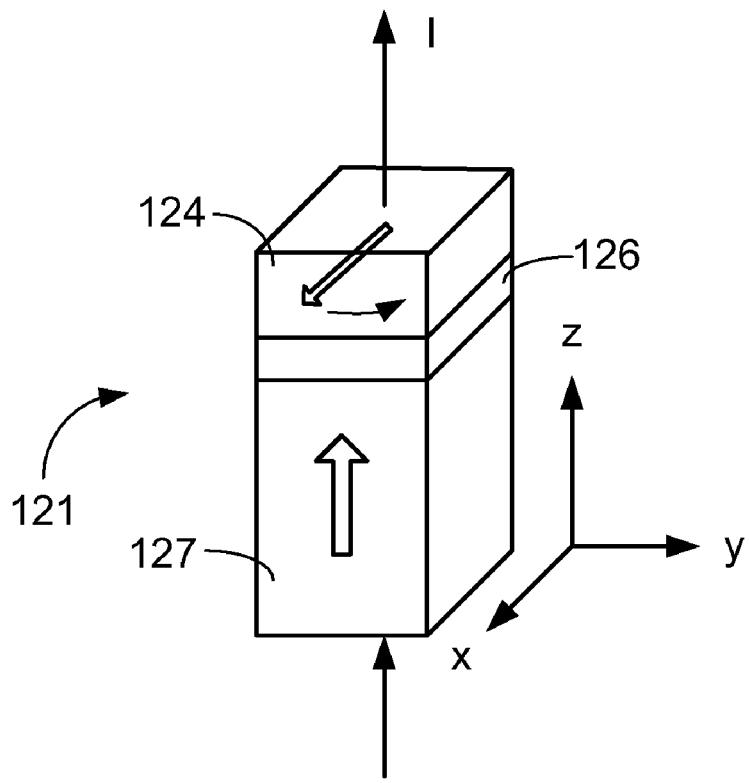
FIG. 4 is a schematic diagram of an exemplary fixed multilayer stack generating a magnetization oscillation.

FIG. 4 is a schematic circuit diagram of an exemplary fixed multilayer stack generating a magnetization oscillation. The fixed multilayer stack 121 includes a nonmagnetic layer 126 separating to magnetic layers 127, 124. The fixed multilayer stack 121 has a thickness direction (z-direction), and length (y-direction) and width (x-direction). A current I (direct current) passes through the thickness direction (z-direction) of the fixed multilayer stack 121 to generate the varying magnetic field. While the fixed multilayer stack 121 is illustrated as an elongated cubic form, the fixed multilayer stack 121 can take any useful shape. In some embodiments, the magnetization in the z-direction can be achieved by shape anisotropy associated with greater z-dimension. In some embodiments, magnetization in the z-direction can be achieved by magnetic anisotropy that is intrinsic to the material. Electrodes (not shown) can be in contact with the ends of the fixed multilayer stack 121 to assist in passing current through the fixed multilayer stack 121. While the fixed multilayer stack 121 can have any useful dimension, these structures can be formed on the nanometer scale.

The nonmagnetic layer 126 is a barrier or spacer layer that has a thickness less than the spin diffusion length. Thus, spin polarization of the current I is conserved when it passes through the nonmagnetic layer 126 into the magnetic layer 124. The nonmagnetic layer 126 may be made of an insulator material such as $Al_2O_3$ or MgO or of a nonmagnetic metal such as Cu. Other suitable materials may also be used.

The magnetic layers 127, 124 may be made of ferromagnetic (FM) alloys such as Fe, Co, Ni. The magnetization direction of one magnetic layer 127 is magnetized (fixed or pinned) in the thickness or z-direction due to shape anisotropy of this element, while the magnetization direction of other magnetic layer 124 is free to rotate under the influence of a spin torque and can be referred to as a "free layer." The first magnetic layer 127 has its magnetization orientation fixed or pinned in a direction perpendicular to the x-y plane of the fixed multilayer stack 121 and the second magnetic layer 124 has its magnetization orientation (rotatable or free) parallel to the x-y plane of the fixed multilayer stack 121. Thus, the first magnetic layer 127 has its magnetization orientation perpendicular to the second magnetic layer 124 magnetization orientation.

When an electron current is injected into the first magnetic layer 127 in the z-direction, it is spin polarized by the first magnetic layer 127. The spin polarization of the current I is conserved when it passes through the nonmagnetic layer 126 into the second magnetic layer 124. Spin transfer torque arises from the s-d interaction between the conductive electrons and the local moments of the magnet. The spin polarized current exerts a torque on the second magnetic layer 124 magnetization orientation and generates a magnetization oscillation. In a form of the magnetization oscillation is the magnetization rotation in the stack plane. Nevertheless, there is a small component of the magnetization precession out of the plane, which can be detected as an AC output voltage.

Figure 5:
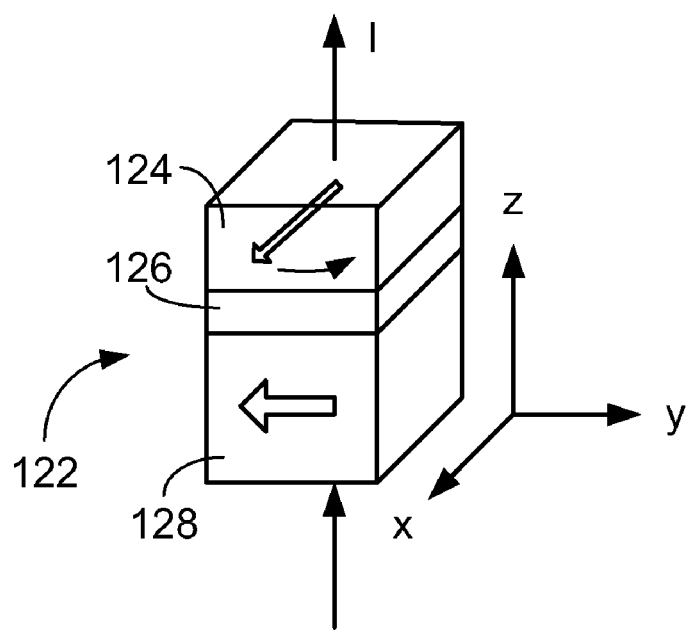
FIG. 5 is a schematic diagram of another exemplary fixed multilayer stack generating a magnetization oscillation.

FIG. 5 is a side view schematic diagram of another exemplary fixed multilayer stack 122 generating a magnetization oscillation. The fixed multilayer stack 122 includes a nonmagnetic layer 126 separating to magnetic layers 128, 124. The fixed multilayer stack 122 has a thickness direction (z-direction), and length (y-direction) and width (x-direction). A spin polarized current I (direct current) passes through the thickness direction (z-direction) of the fixed multilayer stack 122 to generate the magnetization oscillation. While the fixed multilayer stack 122 is illustrated as a cubic form, the fixed multilayer stack 122 can take any useful shape. Electrodes (not shown) can be in contact with the ends of the fixed multilayer stack 122 to assist in passing the spin polarized current through the fixed multilayer stack 122. While the fixed multilayer stack 122 can have any useful dimension, these structures can be formed on the nanometer scale.

The nonmagnetic layer 126 is a barrier or spacer layer that has a thickness less than the spin diffusion length. Thus, spin polarization of the current I is conserved when it passes through the nonmagnetic layer 126 into the magnetic layer 124. The nonmagnetic layer 126 may be made of an insulator material such as $Al_2O_3$ or MgO or of a nonmagnetic metal such as Cu. Other suitable materials may also be used.

The magnetic layers 128, 124 may be made of ferromagnetic (FM) alloys such as Fe, Co, Ni. The magnetization direction of one magnetic layer 128 is magnetized (fixed or pinned) in the a direction parallel to the x-y plane of the fixed multilayer stack 122, while the magnetization direction of other magnetic layer 124 is free to rotate under the influence of a spin torque and can be referred to as a "free layer." The second magnetic layer 124 has its magnetization orientation (rotatable or free) parallel to the x-y plane of the fixed multilayer stack 122. Thus, the first magnetic layer 128 has its magnetization orientation parallel to the second magnetic layer 124 magnetization orientation.

When a spin polarized electron current I is injected into the fixed multilayer stack 122 in the z-direction, the spin polarization of the current I is conserved when it passes through the nonmagnetic layer 126 into the second magnetic layer 124. Spin transfer torque arises from the s-d interaction between the conductive electrons and the local moments of the magnet. The spin polarized current exerts a torque on the second magnetic layer 124 magnetization orientation and generates a magnetization oscillation. The magnetization oscillation can be converted to an AC output voltage for readout.

Figure 6:
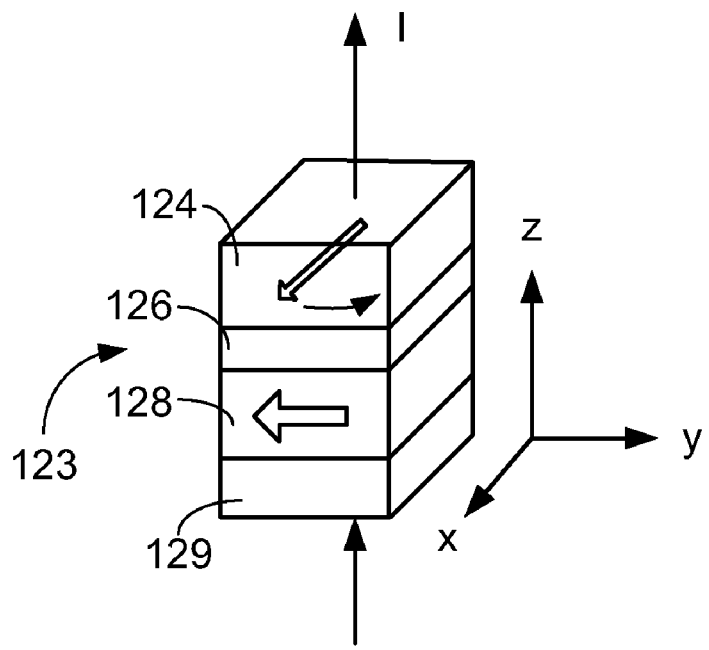
FIG. 6 is a schematic diagram of another exemplary fixed multilayer stack generating a magnetization oscillation.

FIG. 6 is a side view schematic diagram of another exemplary fixed multilayer stack 123 generating a magnetization oscillation. The fixed multilayer stack 123 includes a non-magnetic layer 126 separating to magnetic layers 128, 124. The fixed multilayer stack 123 has a thickness direction (z-direction), and length (y-direction) and width (x-direction). A spin polarized current I (direct current) passes through the thickness direction (z-direction) of the fixed multilayer stack 123 to generate the rotating magnetic field. While the fixed multilayer stack 123 is illustrated as a cubic form, the fixed multilayer stack 123 can take any useful shape. Electrodes (not shown) can be in contact with the ends of the fixed multilayer stack 123 to assist in passing the spin polarized current through the fixed multilayer stack 23. While the fixed multilayer stack 23 can have any useful dimension, these structures can be formed on the nanometer scale.

The nonmagnetic layer 126 is a barrier or spacer layer that has a thickness less than the spin diffusion length. Thus, spin polarization of the current I is conserved when it passes through the nonmagnetic layer 126 into the magnetic layer 124. The nonmagnetic layer 126 may be made of an insulator material such as $Al_2O_3$ or MgO or of a nonmagnetic metal such as Cu. Other suitable materials may also be used.

The fixed multilayer stack 123 also includes a pinning layer 129. The pinning layer 129 is an antiferromagnetic layer. The antiferromagnet has two sublattices of magnetic moments pointing in opposite directions. When a ferromagnetic layer (i.e., magnetic layers 128) is in contact with it, the magnetization of the ferromagnet (i.e., magnetic layers 128) is pinned in a direction. So the antiferromagnetic layer is called pining layer 129 and the ferromagnetic layer is called pinned layer 128.

The magnetic layers 128, 124 may be made of ferromagnetic (FM) alloys such as Fe, Co, Ni. The magnetization direction of one magnetic layer 128 is magnetized (fixed or pinned) in the a direction parallel to the x-y plane of the fixed multilayer stack 122, while the magnetization direction of other magnetic layer 124 is free to rotate under the influence of a spin torque and can be referred to as a "free layer." The second magnetic layer 124 has its magnetization orientation (rotatable or free) parallel to the x-y plane of the fixed multilayer stack 122. Thus, the first magnetic layer 128 has its magnetization orientation parallel to the second magnetic layer 124 magnetization orientation.

When a spin polarized electron current I is injected into the fixed multilayer stack 122 in the z-direction, the spin polarization of the current I is conserved when it passes through the nonmagnetic layer 126 into the second magnetic layer 124. Spin transfer torque arises from the s-d interaction between the conductive electrons and the local moments of the magnet. The spin polarized current exerts a torque on the second magnetic layer 124 magnetization orientation and generates a magnetization oscillation. The magnetization oscillation can be converted into an AC output voltage for readout.

Figure 7:
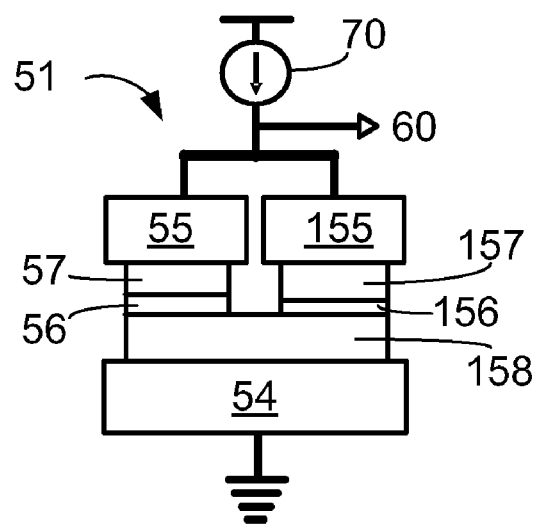
FIG. 7 is a schematic circuit diagram of an exemplary fixed multilayer stack generating a magnetization oscillation.

FIG. 7 is a schematic circuit diagram of another exemplary fixed multilayer stack generating a rotating magnetic field. The illustrated magnetic oscillator 51 includes a two fixed multilayer stacks in parallel electrical connection. The first fixed multilayer stack includes a non-magnetic barrier or spacer layer 56 separating a fixed or pinned magnetic layer 57 and a free magnetic layer 158. The second fixed multilayer stack includes a non-magnetic barrier or spacer layer 156 separating a fixed or pinned magnetic layer 157 and a free magnetic layer 158. In the illustrated embodiment the free layer 158 is a co-extensive layer where the first fixed multilayer stack and the second fixed multilayer stack share the free layer 158. In some embodiments (not shown) the pinned layer 55 and 155 can also be a co-extensive layer where the first fixed multilayer stack and the second fixed multilayer stack share a common pinned layer. The first fixed multilayer stack is electrically between a first electrode 54 and a second electrode 55. The second fixed multilayer stack is electrically between the first electrode 54 and a third electrode 155.

Current is provided by a voltage source 70. The current is a direct current. The magnetic rotation frequency can be readout at an output 60. When a DC current is driven into the fixed multilayer stack (i.e., magnetic pillar), an AC voltage difference with a radio frequency appears across the stack due to the spin-torque transfer effect, that means some kind of magnetization precession is excited by the current in the free layer, which is translated to the AC voltage. When DC current is driven into this structure 51 the two fixed multilayer stacks oscillate (i.e., rotate) at a common frequency with phase lock. A high AC voltage output and quality factor is achieved. When the two fixed multilayer stacks are designed to have different magnetic field dependencies of the each individual oscillation frequency, the phase locking will be lost in the presence of a magnetic nanoparticle tag magnetic field. In detection, the common mode of the oscillation between the nano-oscillators (i.e., fixed multilayer stacks) disappears or greatly diminishes. Therefore, the detection can be described as a digital mode in frequency domain.

Figure 8:
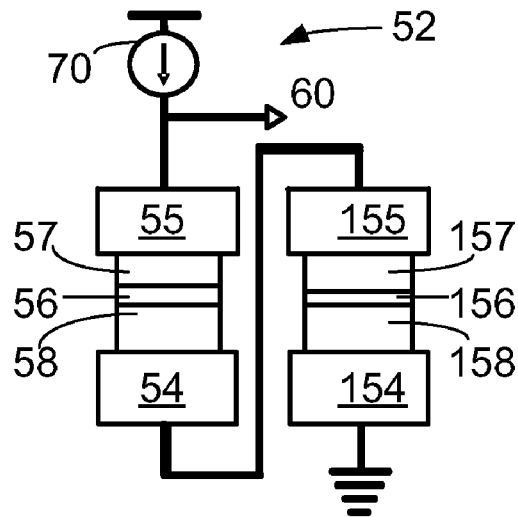
FIG. 8 is a schematic circuit diagram of another exemplary fixed multilayer stack generating a magnetization oscillation.

FIG. 8 is a schematic circuit diagram of another exemplary fixed multilayer stack generating magnetization oscillation. The illustrated magnetic oscillator 52 includes a two fixed multilayer stacks in serial electrical connection. The first fixed multilayer stack includes a non-magnetic barrier or spacer layer 56 separating a fixed or pinned magnetic layer 57 and a free magnetic layer 58. The second fixed multilayer stack includes a non-magnetic barrier or spacer layer 156 separating a fixed or pinned magnetic layer 157 and a free magnetic layer 158. The first fixed multilayer stack is electrically between a first electrode 54 and a second electrode 55. The second fixed multilayer stack is electrically between the third electrode 154 and a fourth electrode 155.

Current is provided by a voltage source 70. The current is a direct current. The magnetic rotation frequency can be readout at an output 60. When a DC current is driven into the fixed multilayer stack (i.e., magnetic pillar), an AC voltage difference with a radio frequency appears across the stack due to the spin-torque transfer effect, that means some kind of magnetization precession is excited by the current in the free layer, which is translated to the AC voltage. When DC current is driven into this structure 52 the two fixed multilayer stacks oscillate (i.e., rotate) at a common frequency with phase lock. A high AC voltage output and quality factor is achieved. When the two fixed multilayer stacks are designed to have different magnetic field dependencies of the each individual oscillation frequency, the phase locking will be lost in the presence of a magnetic nanoparticle tag magnetic field. In detection, the common mode of the oscillation between the nano-oscillators (i.e., fixed multilayer stacks) disappears or greatly diminishes. Therefore, the detection can be described as a digital mode in frequency domain.

Figure 9:
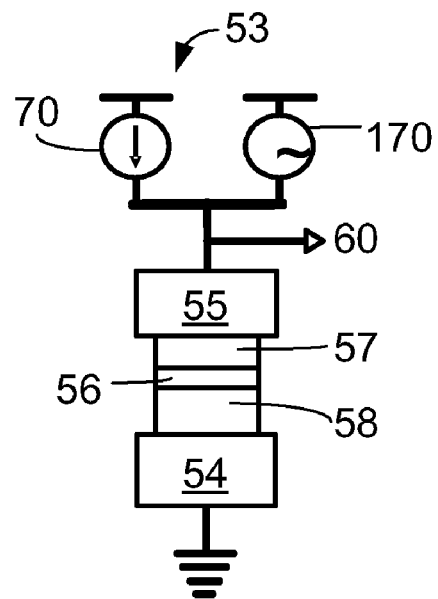
FIG. 9 is a schematic circuit diagram of another exemplary fixed multilayer stack generating a magnetization oscillation.

FIG. 9 is a schematic circuit diagram of another exemplary fixed multilayer stack generating a magnetization oscillation. The illustrated magnetic oscillator 53 includes two current inputs, a direct current voltage source 70 and an alternating current voltage source 170. The fixed multilayer stack includes a non-magnetic barrier or spacer layer 56 separating a fixed or pinned magnetic layer 57 and a free magnetic layer 58. The fixed multilayer stack is electrically between a first electrode 54 and a second electrode 55. The magnetic rotation frequency can be readout at an output 60.

When the intrinsic resonance frequency of the fixed multilayer stack is close to that of the AC input 170, the oscillation is locked by the AC current in frequency and phase. Meanwhile, a high AC voltage output 60 and high quality factor can be achieved. This design is advantageous since the oscillation can be tuned and controlled by the AC current in a small frequency range. On the other hand, the frequency of the AC current can be adjusted according to the intrinsic resonance frequency of the oscillator. The detection is same as for those of FIGS. 8 and 9. Presence of magnetic nanoparticle breaks the frequency and phase locking. Then oscillation will disappear or diminish significantly.

Figure 10:
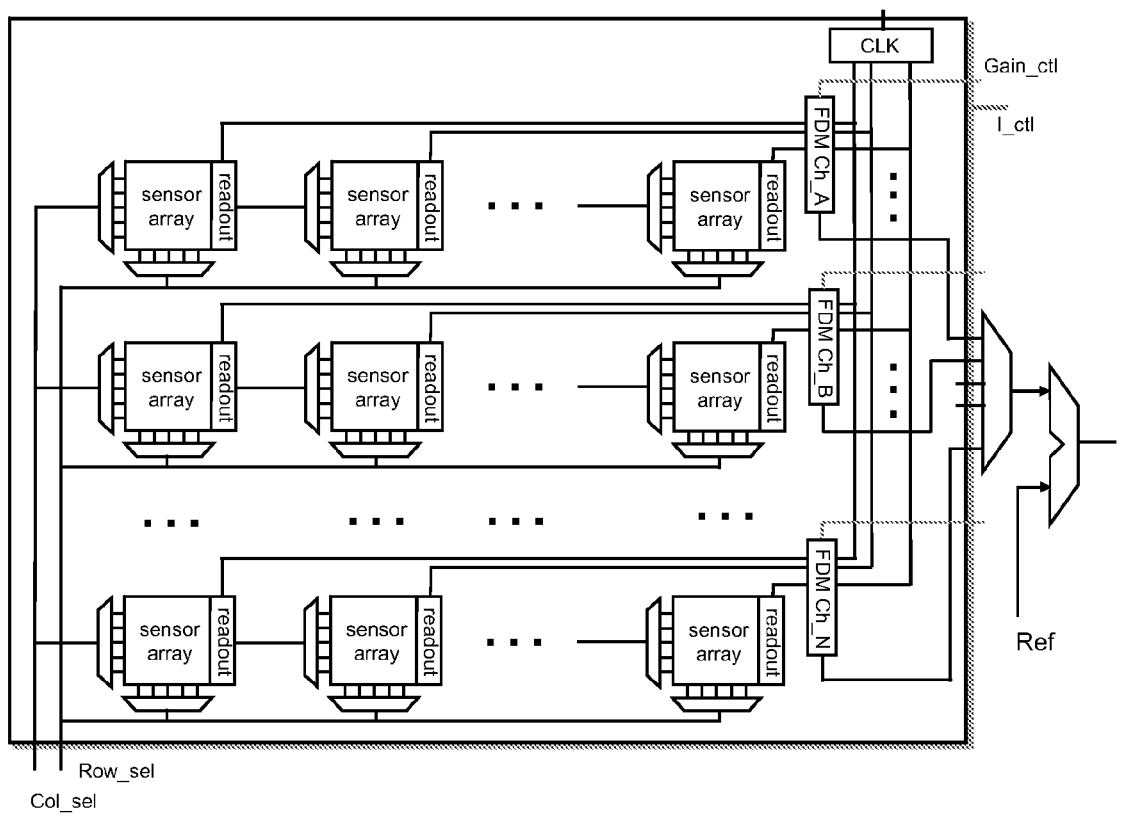
FIG. 10 is a schematic block diagram of a magnetic oscillator biosensor chip architecture.

FIG. 10 is a schematic block diagram of a magnetic oscillator biosensor chip architecture. The biosensor chip consists of many sub-arrays of the biosensors. Each sub-array can have one or more than one fixed multilayer stacks (i.e., magnetic nano-oscillators) as described above. In many embodiments, within a sub-array, the fixed multilayer stacks are designed to have the same oscillation frequency or oscillation frequencies very close to one another for detection. Between sub-arrays, the oscillation frequencies are sufficiently different in order to identify for the DNA spotters, i.e., fixed multilayer stack sub-arrays. A frequency division multiplexing (FDM) scheme is used to reduce the readout time. The output signal is compared with reference frequency for signal detection.

As shown in FIG. 10, the sub-arrays share the same control bus to select the oscillators within a sub-array by Col_sel and Row_sel. The sub-arrays in a row are frequency-division multiplexed to form a channel, FDM Ch_A, FDM Ch_B, . . . or FDM Ch_N. A clock, CLK, is used to generate the carrier frequencies for FDM. The output signals from the FDM channels are then time-division multiplexed (TDM) to further reduce the read-out time. The final output is then compared to a reference to detect the signal. The final output can also be digitized by an analog-digital converter (ADC) that is not shown in the figure. Gain_ctl is used to adjust the gain of the FDM channels. I_ctl is used for the current input to the chip.

Figure 11:
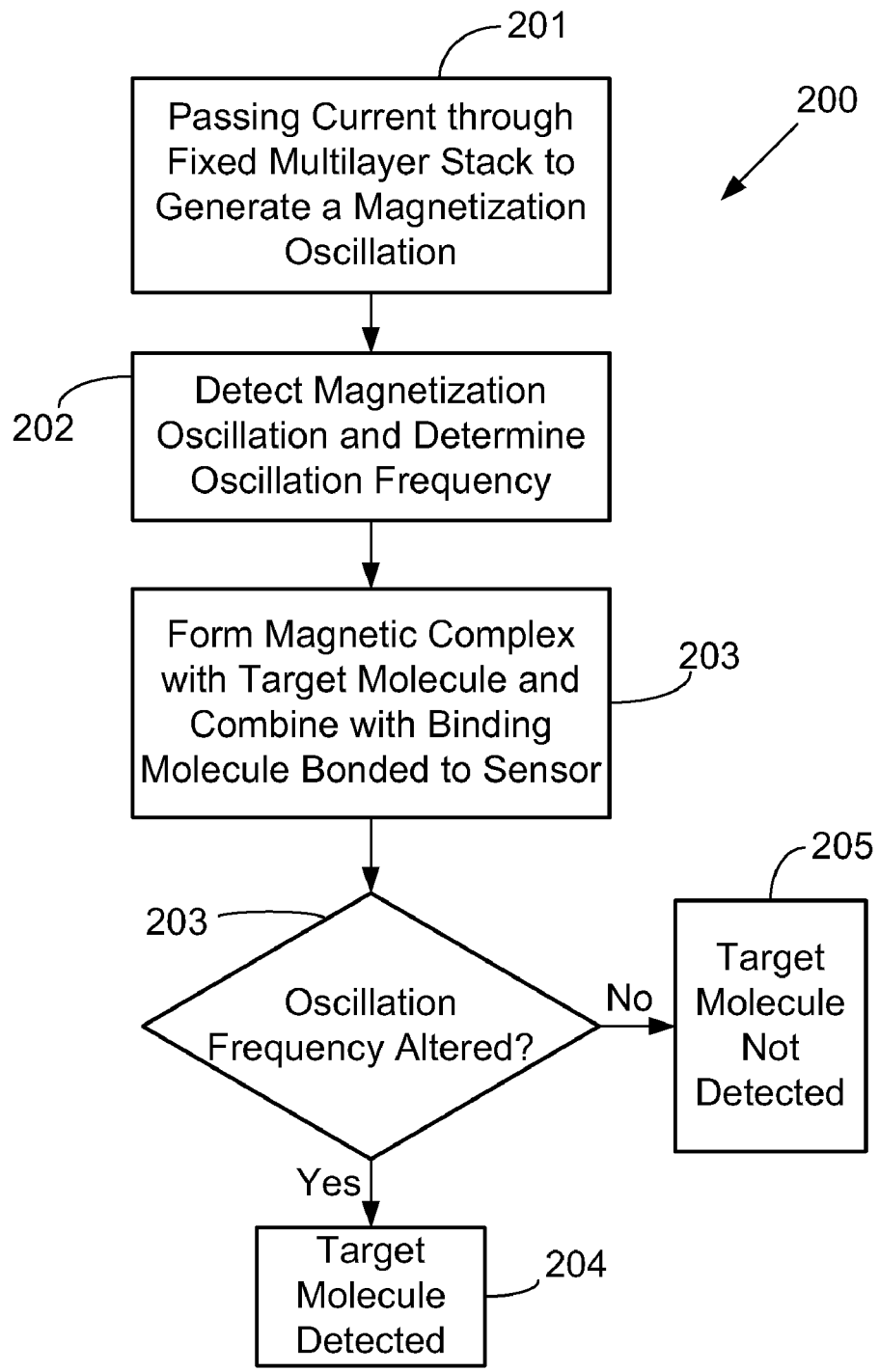
FIG. 11 is a flow diagram of an illustrative method for sensing a target molecule with a magnetic oscillator biosensor.

FIG. 11 is a flow diagram 200 of an illustrative method for sensing a target molecule with a magnetic oscillator biosensor. The method includes passing a current through a fixed multilayer stack to generate magnetization oscillation with the fixed multilayer stack with the current at block 201. Then the magnetization oscillation is detected at block 202. A magnetic complex is formed with a target molecule and combined with a binding molecule that is bonded to the sensor at block 203. Then at decision block 203, if the oscillation frequency is altered then the target molecule is detected at block 204, otherwise the target molecule is not detected at block 205.

Thus, embodiments of the MAGNETIC OSCILLATOR BASED BIOSENSORS are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation, and the present invention is limited only by the claims that follow.

What is claimed is:

1. A biosensor, comprising:
   a multilayer magnetic stack providing a rotating magnetic field;
   a voltage source electrically coupled to the multilayer stack, the voltage source providing a direct current through the multilayer magnetic stack to generate the rotating magnetic field with a spin polarized current;
   a binding molecule bonded to the multilayer magnetic stack, wherein a target molecule comprises a magnetic nanoparticle that forms a complex with the binding molecule and alters the rotating magnetic field.

2. A biosensor according to claim 1, wherein the direct current is the spin polarized current.

3. A biosensor according to claim 1, wherein the multilayer magnetic stack spin polarizes direct current and generates the rotating magnetic field.

4. A biosensor according to claim 1, wherein the multilayer magnetic stack comprises a non-magnetic barrier layer between a first magnetic layer and a second magnetic layer, the first magnetic layer having a first pinned magnetization orientation and the second magnetic layer having a second free magnetization orientation that is orthogonal to the first magnetization orientation.

5. A biosensor according to claim 1, wherein the multilayer magnetic stack comprises a non-magnetic barrier layer between a first magnetic layer and a second magnetic layer, the first magnetic layer having a first pinned magnetization orientation plane and the second magnetic layer having a second free magnetization orientation plane that is parallel to the first magnetization orientation plane.

6. A biosensor according to claim 1, wherein the target molecule is covalently bonded to the multilayer magnetic stack.

7. A biosensor according to claim 1, further comprising a second multilayer magnetic stack electrically coupled to the voltage source and the multilayer magnetic stack in parallel.

8. A biosensor according to claim 1, further comprising a second multilayer magnetic stack electrically coupled to the voltage source and the multilayer magnetic stack in series.

9. A biosensor according to claim 1, wherein the voltage source further comprises an alternating current voltage source.

10. A biosensor according to claim 1, wherein the multilayer magnetic stack is electrically between a first electrode and a second electrode, the first electrode and the second electrode providing an electrical path for the direct current.

11. A biosensor array comprising:
    a plurality of detection sites disposed on a substrate; and
    a voltage source electrically coupled to the detection sites, the voltage source providing a direct current to the detection sites;
    wherein at least selected detection sites comprise:
      a multilayer magnetic stack generating a rotating magnetic field upon passing a spin polarized direct current through the multilayer magnetic stack; and
      a binding molecule covalently bonded to the multilayer magnetic stack, wherein a target molecule comprises a magnetic nanoparticle that forms a complex with the binding molecule and alters the rotating magnetic field.

12. A biosensor array according to claim 11, wherein the plurality of detection sites is subdivided into sub-arrays and at least selected sub-arrays have different types of binding molecules.

13. A biosensor array according to claim 11, wherein the plurality of detection sites is subdivided into sub-arrays and at least selected sub-arrays have different oscillation frequencies.

14. A biosensor array according to claim 11, wherein the multilayer magnetic stack spin polarizes direct current and generates the rotating magnetic field.

15. A biosensor array according to claim 11, further comprising a second multilayer magnetic stack electrically coupled to the voltage source, and the multilayer magnetic stack is in parallel connection with the second multilayer magnetic stack.

16. A biosensor array according to claim 11, further comprising a second multilayer magnetic stack electrically coupled to the voltage source, and the multilayer magnetic stack is in serial connection with the second multilayer magnetic stack.

17. A biosensor array according to claim 11, wherein the voltage source further comprises an alternating current voltage source.

18. A method of detecting a magnetic complex in a sample, comprising steps of:

passing a spin polarized direct current through a multilayer magnetic stack;

generating a rotating magnetic field in the multilayer magnetic stack with the spin polarized direct current;

detecting the rotating magnetic field;

forming a magnetic complex between a target molecule, comprising a magnetic nanoparticle located in a sample, and a binding molecule covalently bonded to the multilayer magnetic stack; and detecting if the rotating magnetic field has been altered with the magnetic complex to form an altered rotating magnetic field to determine the presence of the target molecule in the sample.

19. A method according to claim 18, wherein the multilayer magnetic stack comprises a non-magnetic barrier layer between a first magnetic layer and a second magnetic layer, the first magnetic layer having a first pinned magnetization orientation and the second magnetic layer having a second free magnetization orientation that is orthogonal to the first magnetization orientation and the multilayer magnetic stack spin polarizes direct current and generates the rotating magnetic field.

20. A method according to claim 18, wherein the multilayer magnetic stack comprises a non-magnetic barrier layer between a first magnetic layer and a second magnetic layer, the first magnetic layer having a first pinned magnetization orientation plane and the second magnetic layer having a second free magnetization orientation plane that is parallel to the first magnetization orientation plane.

\* \* \* \* \*